(12) United States Patent
Wang et al.

(10) Patent No.: US 12,329,285 B2
(45) Date of Patent: Jun. 17, 2025

(54) BED WITH VIBROACOUSTIC THERAPY SYSTEM

(71) Applicant: Nisco Co., Ltd, Jiangsu (CN)

(72) Inventors: Wei Wang, Jiangsu (CN); Jian Xie, Jiangsu (CN)

(73) Assignee: NISCO CO., LTD, Jiangsu (CN)

( * ) Notice: Subject to any disclaimer, the term of this patent is extended or adjusted under 35 U.S.C. 154(b) by 1091 days.

(21) Appl. No.: 17/238,371

(22) Filed: Apr. 23, 2021

(65) Prior Publication Data

US 2022/0117401 A1    Apr. 21, 2022

(30) Foreign Application Priority Data

Oct. 15, 2020   (CN) ...................... 2020222895563.0

(51) Int. Cl.
| | |
|---|---|
| *A47C 21/00* | (2006.01) |
| *A47C 20/04* | (2006.01) |
| *A47C 31/00* | (2006.01) |
| *A61H 1/00* | (2006.01) |
| *A61H 23/02* | (2006.01) |
| *A61M 21/00* | (2006.01) |
| *A61M 21/02* | (2006.01) |

(52) U.S. Cl.
CPC .......... *A47C 21/006* (2013.01); *A47C 20/041* (2013.01); *A47C 31/008* (2013.01); *A61H 1/005* (2013.01); *A61M 21/02* (2013.01); *A61H 2201/0142* (2013.01); *A61H 2201/5002* (2013.01); *A61H 2201/5097* (2013.01); *A61M 2021/0022* (2013.01); *A61M 2021/0027* (2013.01)

(58) Field of Classification Search
CPC ... A47C 21/006; A47C 20/041; A47C 31/008; A61H 1/005; A61H 2201/0142; A61H 2201/5002; A61H 2201/5097; A61H 23/0236; A61H 2201/5015; A61H 2201/5043; A61M 21/02; A61M 2021/0022; A61M 2021/0027
See application file for complete search history.

(56) References Cited

U.S. PATENT DOCUMENTS

2008/0052830 A1 *   3/2008   Koughan .............. A47C 19/005
                                                                 5/660
2020/0107646 A1 *   4/2020   Sherman .............. A47C 21/006

FOREIGN PATENT DOCUMENTS

CN            205994075 U      3/2017

* cited by examiner

*Primary Examiner* — Carrie R Dorna
*Assistant Examiner* — Joshua Daryl D Lannu
(74) *Attorney, Agent, or Firm* — troutman pepper locke; Tim Tingkang Xia, Esq.

(57) ABSTRACT

A bed with a vibroacoustic therapy system that combines the relaxation power of body sonic energy massage, soothing low-frequency sound waves, and the healing power of users' favorite music to deliver the ultimate in stress reduction, pain relief, increases of circulation and mobility for the users. The bed includes a frame structure; a plurality of platforms disposed on the frame structure; and one or more massage devices spatial-separately installed on the plurality of platforms. The one or more massage devices comprises sonic vibrators or music based vibrators. The one or more massage devices are operable individually or cooperatively with a remote control, and/or a smart mobile device.

15 Claims, 10 Drawing Sheets

BED WITH VIBROACOUSTIC THERAPY SYSTEM

CROSS-REFERENCE TO RELATED PATENT APPLICATION

This application claims priority to and the benefit of Chinese Patent Application Nos. 202022289556.0 filed Oct. 15, 2020, which is incorporated herein in its entirety by reference.

FIELD OF THE INVENTION

The invention generally relates to a bed, and more particular to a bed with a vibroacoustic therapy system.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

More and more people are experiencing in increase of pressure and decrease of sleep quality with the fast pace of modern life, which causes insomnia and their physical fitness. Most people still use old-fashioned beds. Old-fashioned beds have problems such as the inability to adjust the spine of the body and relax the body.

In order to properly adjust the body spine and relax the body of the user so as to effectively relieve pressure and improve the sleep quality, beds with massage functions are available. A typical massage bed has small sound boxes and vibration motors built into the mattress. For example, Chinese Utility Mode Patent No. CN205994075U describes an electric music massage bed including a mattress having the built-in small speakers or sound boxes and multiple small vibration motor embedded therein. Such an installation method requires that the space for the sound boxes and motor installation is reserved when the mattress is manufactured. For most mattresses, the internal structure is relatively soft, when installing hard parts such as speakers and motors inside, it is very troublesome for the fixing of the speakers and motors. The motors may be easily displaced inside the mattress. Additionally, if the thickness of the mattress is relatively thin, the user may be affected by the installed speakers and motors when lying on the mattress.

Therefore, a heretofore unaddressed need exists in the art to address the aforementioned deficiencies and inadequacies.

SUMMARY OF THE INVENTION

One of the objectives of the invention is to provide a bed with a vibroacoustic therapy system that combines the relaxation power of body sonic energy massage, soothing low-frequency sound waves, and the healing power of users' favorite music to deliver the ultimate in stress reduction, pain relief, increases of circulation and mobility.

In one aspect of the invention, the bed includes a frame structure; a plurality of platforms disposed on the frame structure; and one or more massage devices spatial-separately installed on the plurality of platforms, wherein each massage device comprises a sonic vibrator. The sonic vibrator is a music based vibrator capable of being activated by music.

In one embodiment, the one or more massage devices are operable individually or cooperatively.

In one embodiment, the one or more massage devices are operable with a remote control, and/or a smart mobile device.

In one embodiment, the sonic vibrator is accommodated in an opening defined in a respective platform of the plurality of platforms through a transition piece fixed on the respective platform.

In one embodiment, the transition piece has a through hole and one or more protrusions on an inner wall of the through hole, and wherein the sonic vibrator has a bottom flange mounted on the one or more protrusions of the transition piece.

In one embodiment, the transition piece is capable of vibrating up and down with the sonic vibrator.

In one embodiment, the transition piece is an elastic soft plate formed of rubber or silicone, or a hard thin sheet formed of aluminum, steel, or wooden composite.

In one embodiment, the bed further comprises a lifting mechanism positioned between the frame structure and the plurality of platforms for operably adjusting positions of at least one of the plurality of platforms so as to adjust the bed at a desired position.

In one embodiment, the lifting mechanism comprises a pair of lifting assemblies. Each lifting assembly comprises a bracket mounted on the frame structure; a back lifting arm and a leg lifting mechanism; and a back lifting actuator and a leg lifting actuator received in the bracket. Each of the back and leg lifting actuators comprises a driving shaft and a motor member engaged with the driving shaft for driving the driving shaft to rotate. The driving shaft of the back lifting actuator is engaged with the back lifting arm for operably adjusting the back lifting arm at desired back positions. The driving shaft of the leg lifting actuator is engaged to the leg lifting mechanism for operably adjusting the leg lifting mechanism at desired leg positions.

In one embodiment, the bed further comprises a positioning bar attached to the back lifting arm and adapted such that when the bed is in a laid back position, the positioning bar in cooperation with the back lifting arm is positioned against the frame structure so as to provide support thereto.

In one embodiment, the leg lifting mechanism comprises first, second, and third leg supporting members. The first leg supporting member is connected to the driving shaft of the leg lifting actuator, the second leg supporting member is pivotally connected to the first leg supporting member, the third supporting member is pivotally connected to the second leg supporting member and the frame structure.

In one embodiment, the bed further comprises at least one supporting bar attached to the frame structure and corresponding to the first leg supporting member, such that when the bed is in a laid back position, the at least one supporting bar is against the first leg supporting member so as to provide support thereto.

In one embodiment, the plurality of platforms comprises a seat platform mounted on tops of the brackets of the pair of lifting assemblies; at least one back platform coupled with the back lifting arm, such that the at least one back platform is operably rotatable around its lower edge in a back platform downward rotating direction or a back platform upward rotating direction; and a thigh platform and a leg platform coupled to the leg lifting mechanism, such that the thigh platform is rotatable around its upper edge in a thigh platform downward rotating direction or a thigh platform upward rotating direction, and the leg platform is rotatable around its upper edge in a leg platform downward rotating direction or a leg platform upward rotating direction.

In one embodiment, the lifting mechanism comprises a back lifting assembly and a leg lifting assembly. The back lifting assembly comprises a back lifting bracket pivotally connected to the frame structure, and a back lifting actuator pivotally connected between the back lifting bracket and the frame structure for operably driving the back lifting bracket to pivotally move in an upward rotating direction or a downward rotating direction relative to the frame structure. The leg lifting assembly comprises a leg lifting bracket pivotally connected to the frame structure, and a leg lifting actuator pivotally connected between the leg lifting bracket and the frame structure for operably driving the leg lifting bracket to pivotally move in an upward rotating direction or a downward rotating direction relative to the frame structure.

In one embodiment, the back lifting actuator comprises a motor member, an outer tube extending from the motor member, and an activation rod having a first end portion received in the outer tube and an opposite, second end portion, wherein the activation rod is engaged with the motor member and configured to be telescopically movable relative to the outer tube according to a direction of motor rotation, wherein the motor member is pivotally connected to the frame structure and the second end portion of the activation rod pivotally connected to the back lifting bracket, or wherein the motor member is pivotally connected to the back lifting bracket and the second end portion of the activation rod pivotally connected to the frame structure.

In one embodiment, the leg lifting actuator comprises a motor member, an outer tube extending from the motor member, and an activation rod having a first end portion received in the outer tube and an opposite, second end portion, wherein the activation rod is engaged with the motor member and configured to be telescopically movable relative to the outer tube according to a direction of motor rotation, wherein the motor member is pivotally connected to the frame structure and the second end portion of the activation rod pivotally connected to the leg lifting bracket, or wherein the motor member is pivotally connected to the leg lifting bracket and the second end portion of the activation rod pivotally connected to the frame structure.

In one embodiment, the bed further comprises a controller configured to control operations of the one or more massage devices and the lifting mechanism so as to provide massage effect from the one or more massage devices and/or adjust positions of the at least one of the plurality of platforms.

Among other things, the invention has the following advantages: the sonic vibrators are directly installed on the bed platforms/boards, which makes the installation and disassembly very convenient, compared to the built-in installation in conventional beds. In addition, the installation of the sonic vibrators uses transitional connection of transition pieces/plates and matches the design of grooves or through holes on the bed platforms/boards, so that the sonic vibrators can still vibrate up and down after installation, realize the massage effects, and provide users with comfortability.

Both a music based vibrators and a transition piece/plate are fixed to each other by bolts, which is convenient for the installation and disassembly and improves the assembly efficiency.

For the connection between a music based vibrator and a transition piece/plate, the through hole corresponding to the music vibrator is opened on the transition piece, thereby reducing the contact area between the music vibrator and the transition piece to improve the vibration of the music vibrator, so as to improve the user's comfort.

The positioning bar/rod is designed to cooperate with the back lifting arm/rod. When the back lifting arm is turned to the horizontal state (a laid back position of the bed), the position of the back lifting arm is positioned and limited to ensure that the turning of the back lifting arm is in place and correct. The frame structure supports the back lifting arm so as to prevent the back lifting arm from turning too low and affecting the user's normal lying down.

The supporting bar/rod is designed to cooperate with the first leg supporting member. When the first leg supporting member is turned to the horizontal state, the first leg supporting member is supported by the supporting bar to prevent the first leg supporting member from turning too low and affecting the user's normal operation.

These and other aspects of the invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
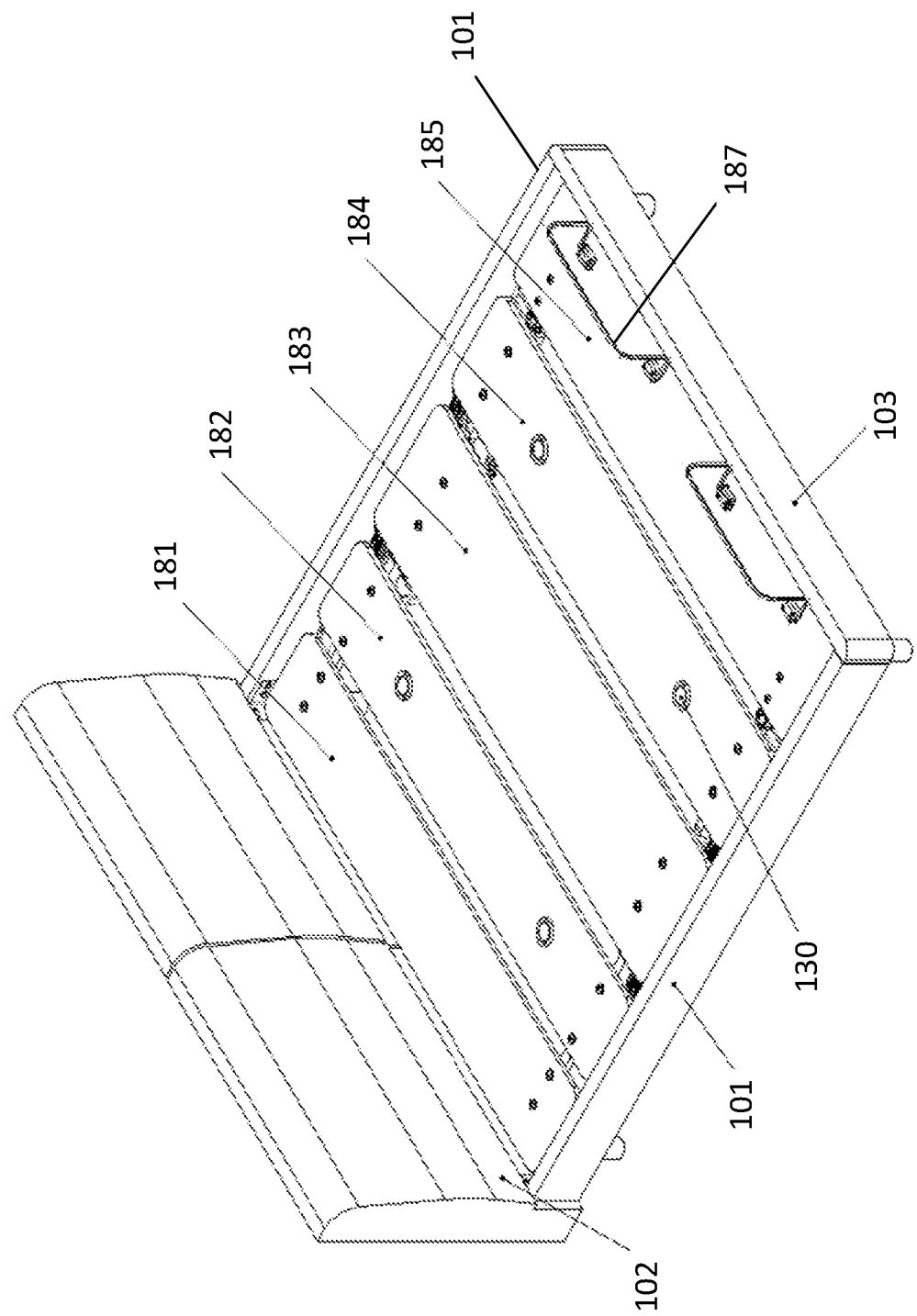
FIG. 1 shows schematically a perspective view of a bed according to one embodiment of the invention.
Figure 2:
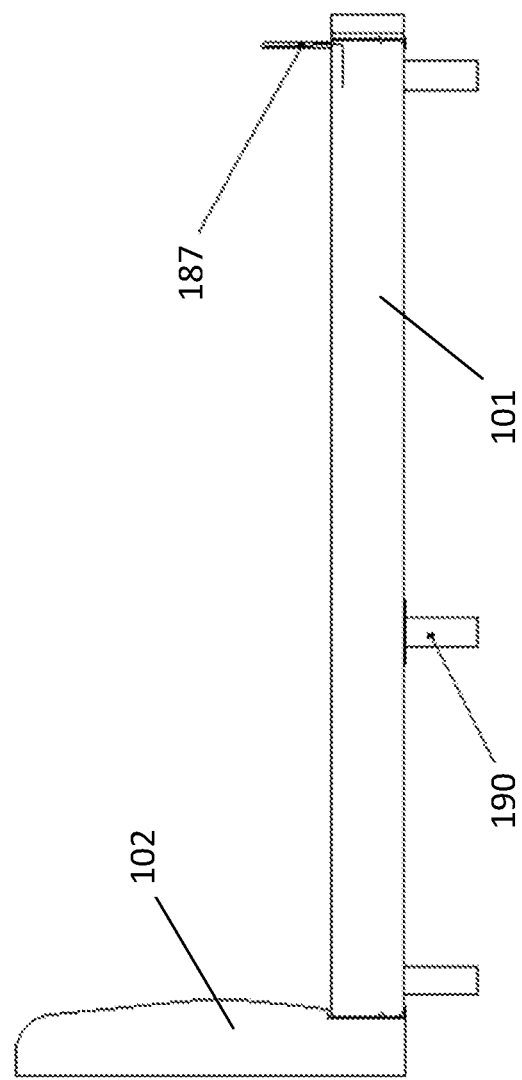
FIG. 2 shows schematically a side view of the bed shown in FIG. 1.

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

The terminology used herein is for the purpose of describing particular embodiments only and is not intended to be limiting of the invention. As used herein, the singular forms "a," "an," and "the" are intended to include the plural forms as well, unless the context clearly indicates otherwise.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present invention.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprise(s)" and/or "comprising," or "include(s)" and/or "including" or "has (have)" and/or "having" or "contain(s)" and/or "containing" when used in this specification specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the term "platform" refers to a bed board.

As used in this specification, the phrase "at least one of A, B, and C" should be construed to mean a logical (A or B or C), using a non-exclusive logical OR. As used herein, the term "and/or" includes any and all combinations of one or more of the associated listed items.

Embodiments of the invention are illustrated in detail hereinafter with reference to accompanying drawings. The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

The description will be made as to the embodiments of the invention in conjunction with the accompanying drawings in FIGS. 1-10. In accordance with the purposes of this invention, as embodied and broadly described herein, this invention, in one aspect, relates to a bed with a vibroacoustic therapy system that combines the relaxation power of body sonic energy massage, soothing low-frequency sound waves, and the healing power of users' favorite music to deliver the ultimate in stress reduction, pain relief, increases of circulation and mobility.

FIGS. 1-7 show the bed with a vibroacoustic therapy system according to one embodiment of the invention. The bed is an electrically-driven adjustable bed. The vibroacoustic therapy system includes, but is not limited to, one or more massage devices, each of which is a music based vibrator capable of being activated by music and sonic wave.

Figure 5:
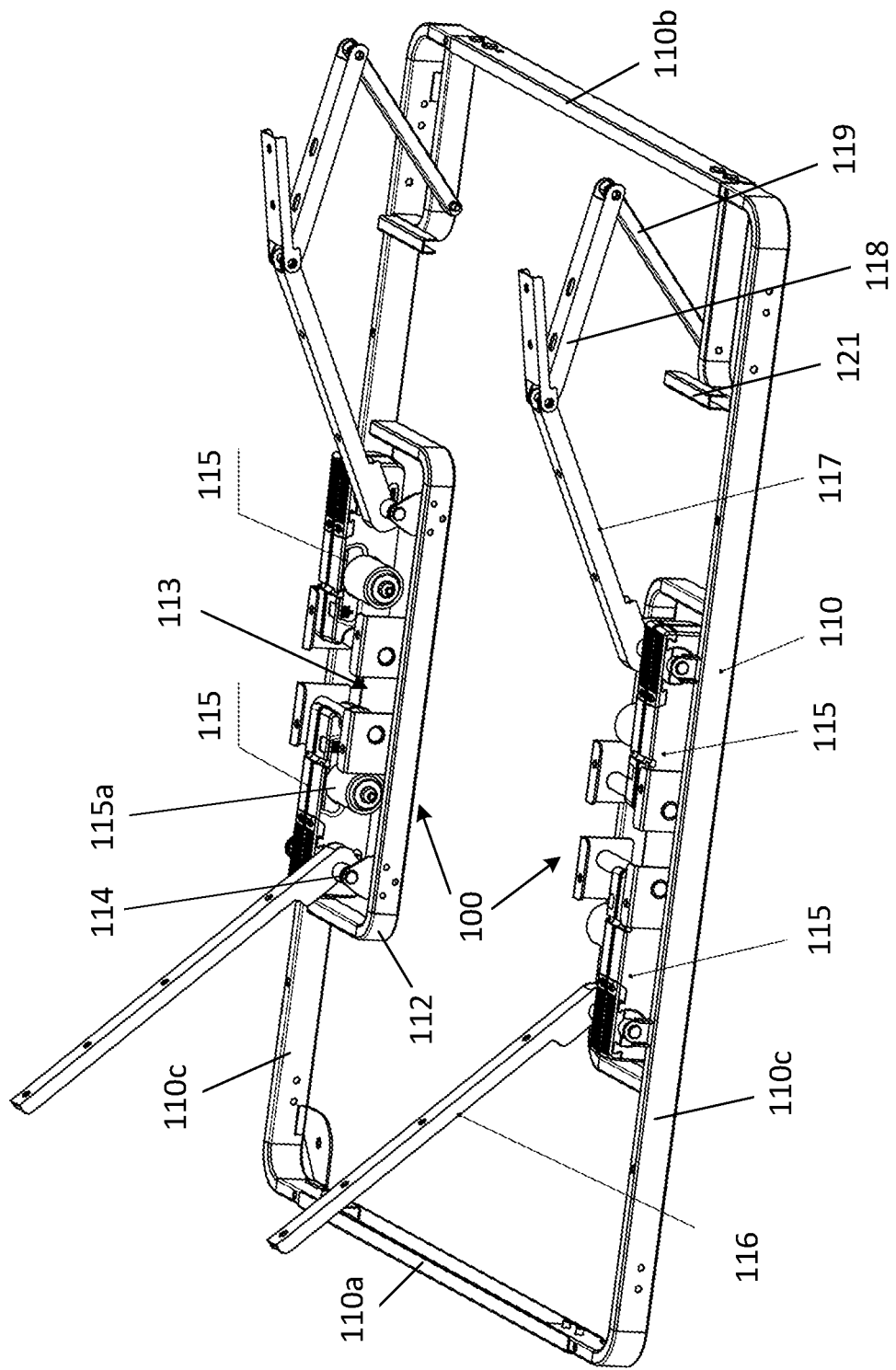
FIG. 5 shows schematically a perspective view of a frame structure and a lifting mechanism of a bed according to one embodiment of the invention.

The bed includes a frame structure 110. The frame structure 110 is a rectangular frame structure including an upper rail/rod 110a and a lower rail/rod 110b that are longitudinally spaced and transversely aligned, and a pair of side rails/rods 110c that is transversely spaced, longitudinally aligned and arranged parallel to each other. Two ends of the upper rail 110a are connected to the first ends of the pair of side rails 110c; two ends of the lower rail 110b are connected to the second ends of the pair of side rails 110c, as shown in FIG. 5, for example.

A number of bed legs/posts 190 are installed at the bottom of the frame structure 110 to support the frame structure 110. The bed legs 190 in some embodiments are mounted on the frame structure 110 by bolts or screws.

As shown in FIG. 1, each outer side of the side rails 110c is provided with a sideboard 101. The outer side of the upper rail 110a is provided with a headboard 102, while the outer side of the lower rail 110b is provided with a footboard 103. The frame structure 110, the sideboard 101, the headboard 102 and the footboard 103 constitute a base frame of the massage bed.

In addition, the bed also includes a plurality of platforms (or bed boards) 181-185 disposed on the frame structure 110. The plurality of platforms includes a head platform/board 181, a back platform/board 182, a seat or waist platform/board 183, a thigh platform/board 184, a leg platform/board 185, orderly disposed on the pair of side rails 110c along the direction from the upper rails 110a to the lower rails 110b. The waist board 4 is fixed on the frame structure 110, while the head board 181, the back platform 182, the thigh platform 184 and the leg platform 185 are movably disposed on the frame structure 110. There is a gap between the back platform 182, the waist platform 183, the thigh platform 184, and the leg platform 185. Further, a pair of baffles 187 are also attached to the leg platform 185. The design of the baffles 187 can limit the position of the mattress when placed on the bed platforms so as to prevent the mattress from sliding on the bed platforms.

Moreover, the bed includes a vibroacoustic therapy system including one or more massage devices 130 spatial-separately installed on the plurality of platforms. Each massage device massage device 130 comprises a sonic (wave) vibrator. The sonic vibrator is a music based vibrator capable of being activated by music and sonic wave. The sonic vibrator may include a sound box and one or more vibration motors. As used in the disclosure, the terms "sonic vibrator", "sonic wave vibrator", "music based vibrator" and "music vibrator" are exchangeable and refer to a massage device or a vibroacoustic therapy device that can produce vibrations in accordance with sonic waves such as music and pass the vibrations into the user's body. One exemplary example of the massage device or the vibroacoustic therapy device is, but is not limited to, a device with embedded speakers. In other embodiments, the vibroacoustic therapy system may also individual speakers that are separated from and synchronized with the sonic vibrators, so that the sonic vibrators can generate massage effects based on the music played by the speakers. The speakers can be wirelessly controllable speakers, such as wireless Bluetooth® speakers, or speakers being capable of connecting to the internet. The individual speakers may be placed at different locations of a bedroom for providing customized vibroacoustic therapy based on the preference of the user.

In some embodiments, the one or more massage devices 130 are operable individually or cooperatively. In one embodiment, the one or more massage devices 130 are operable with a remote control, and/or a smart mobile device. In one embodiment, each sonic vibrator 130 is accommodated in an opening defined in a respective platform of the plurality of platforms through a transition piece fixed on the respective platform.

In the exemplary embodiments shown in FIGS. 1, 3, and 6-8, there are four music vibrators 130 in total, of which two music vibrators 130 are installed on the back platform 182, and the other two music vibrators 130 are installed on the thigh platform 184. Such arrangements allows for improving relaxation of the thighs and back of the user. It should be appreciated that other numbers of music vibrators can also be utilized to practice the invention, and the music vibrators can also be installed on the other platforms.

In the embodiments, the transition connection mechanism is used to install the music vibrators 130 on the platforms. The transition connection mechanism includes a transition piece 131 that is attached to the back platform 182 or the thigh platform 184. The back platform 182 and the thigh platform 184 are also provided with through holes 150 for installation of the music vibrators 130 and accommodation of vibrations generated from the music vibrators 130 when activated. The transition piece 131 is fixed on the bottom surface of the back platform 182 or the thigh platform 184 by bolts/screws, and corresponding threaded blind holes are also opened on the bottom surface of the back platform 182 or the thigh platform 184.

Figure 4A:
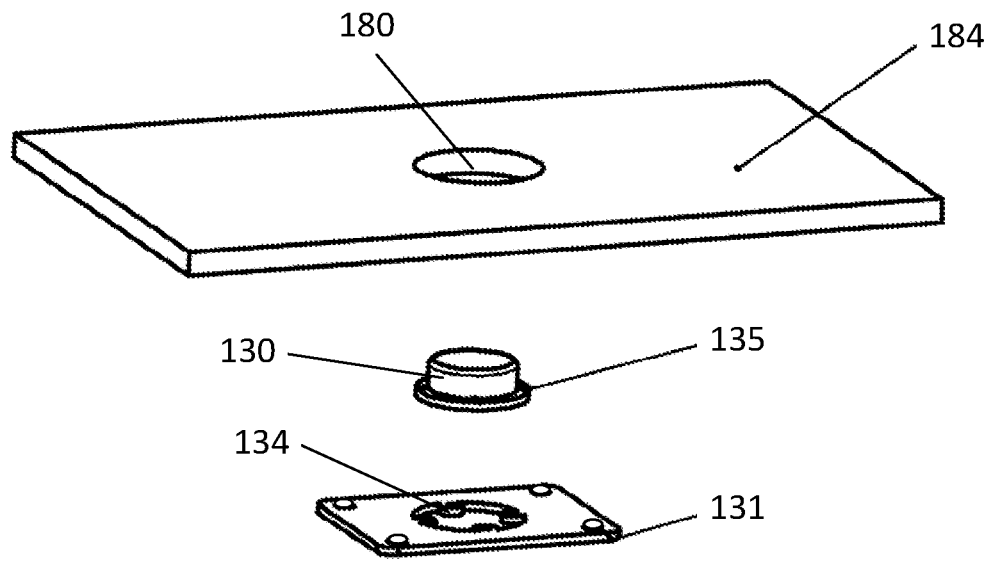
FIGS. 4A-4B show schematically exploded views of a massage device and its installation to a bed platform/board in a bed according to one embodiment of the invention.
Figure 4B:
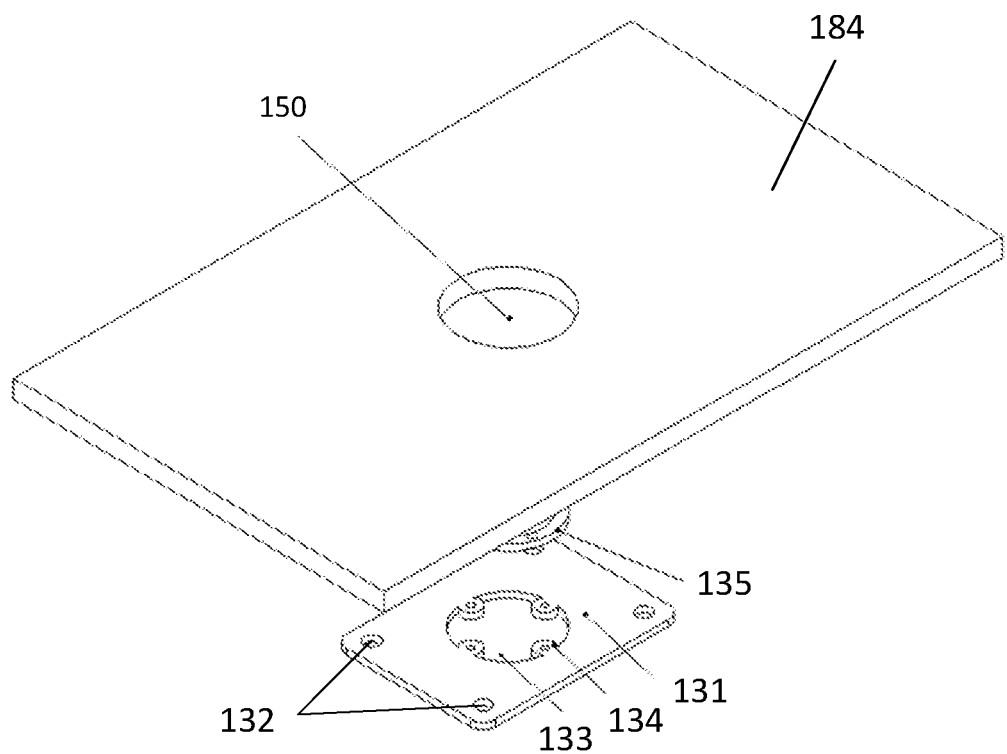

As shown in FIGS. 4A-4B, the transition piece 131 has a through hole 133 for receiving the music vibrator 130 and one or more protrusions 134 on an inner wall of the through hole 133 for mounting the music vibrator 130. The music vibrator 130 has a bottom flange 135 to be mounted on the one or more protrusions 134 of the transition piece 131. Specifically, each protrusion 134 has a first connection hole, and the flange 135 of the music vibrator 130 has a number of second connection holes, where each connection hole is corresponding to the first connection hole of the respective protrusion 134 of the transition piece 131. As assembled, a bolt or screw passes through the first connection hole of the transition piece 131 and the corresponding second connection hole of the music vibrator 130 and is then locked with a nut, so that the music vibrator 130 and the transition piece 131 are fixed to each other. As shown in such embodiments, the connection between the music vibrator 130 and the transition piece 131 is achieved by opening a through hole corresponding to the music vibrator 130 on the transition piece 131, thereby reducing the contact area between the music vibrator 130 and the transition piece 131 to improve the music vibrator 130. The vibration effect improves the user's comfort.

The transition piece 131 can be an elastic soft plate or a hard thin plate that can vibrate up and down with the music vibrator 130. The elastic soft plate can be a rubber sheet such as silicone rubber or rubber, and the hard thin plate can be a thin aluminum plate/film, a thin steel plate/film, other metal plate/film, wooden composite plate/film, or the likes.

According to embodiments of the invention, the music vibrators 130 are directly installed on the bed platforms/boards, where the conventionally built-in installation of vibrators is changed to an external installation, which makes the installation and disassembly very convenient for the installation of the music vibrators 130. The transitional connection of the transitional connecting plate 31 is used in conjunction with the design of the grooves or through holes on the bed platforms/boards, so that the music vibrators 130 can still vibrate up and down after installation, realize the massage function and provide the user with comfort.

The bed further comprises a lifting mechanism positioned between the frame structure 110 and the plurality of platforms 181-185 for operably adjusting positions of at least one of the plurality of platforms 181-185 so as to adjust the bed at a desired position.

Referring to FIG. 5, for example, the lifting mechanism comprises a pair of lifting assemblies 100 with each mounted on the respective side rail 110c of the frame structure 110. The pair of lifting assemblies 100 operates cooperatively to adjust the plurality of platforms 181-185 at the desired positions. Each lifting assembly 100 comprises a bracket 112 mounted on the frame structure 110 and located below the waist board 183. The bracket 112 is a U-shaped bracket amounted on one side rails 110c of the frame structure 110 to form an installation space 113 for a respective lifting assembly 100.

Each lifting assembly 100 also includes a back lifting arm 116 and a leg lifting mechanism; and a pair of lifting actuators (a back lifting actuator and a leg lifting actuator) 115 received in and secured on the bracket 112. Each of the back and leg lifting actuators 115 comprises a driving shaft 114 hinged with s side rail 110c of the frame structure 110 and the bracket 112 and a motor member 115a engaged with the driving shaft 114 for driving the driving shaft 114 to rotate. The driving shaft 114 of the back lifting actuator 115 is engaged with the back lifting arm 116 for operably adjusting the back lifting arm 116 at desired back positions. The driving shaft 114 of the leg lifting actuator 115 is engaged to the leg lifting mechanism for operably adjusting the leg lifting mechanism at desired leg positions.

According to embodiments of the invention, the head and back platforms 181-182 are coupled with the back lifting arm 116 such that the head and back platforms 181-182 are operably rotatable around its lower edge in a back platform downward rotating direction or a back platform upward rotating direction. Specifically, the back lifting arm 116 is engaged with to the driving shaft 114 of the back lifting actuator 115 and extends below the head platform 181. The head platform 181 and the back platform 182 are both fixed on the back lifting arm 116, and the back lifting arm 116 drives the head platform 181 and the back platform 182 to turn at a desired position at the same time.

The leg lifting mechanism comprises first, second, and third leg supporting members 117, 118 and 119. The first leg supporting member 117 is connected to the driving shaft 114 of the leg lifting actuator 115, the second leg supporting member 118 is pivotally connected to the first leg supporting member 117, and the third supporting member 119 is pivotally connected to the second leg supporting member 118 and the frame structure 110. According to embodiments of the invention, the thigh platform 184 and the leg platform 185 are coupled to the leg lifting mechanism, such that the thigh platform 185 is rotatable around its upper edge in a thigh platform downward rotating direction or a thigh platform upward rotating direction, and the leg platform 185 is rotatable around its upper edge in a leg platform downward rotating direction or a leg platform upward rotating direction. Specifically, the first leg supporting member 117 extends below the thigh platform 184 and is connected to the rotating rod 114 at one end. The thigh platform 184 is fixed on the first leg supporting member 117. As such, the first leg supporting member 117 operably drives the thigh platform 184 to turn at a desired position. At the bottom of the leg platform 185, the second leg supporting member 118 corresponding to the first leg supporting member 117 is also installed. Specifically, one end of the second leg supporting member 118 is hinged with another end of the first leg supporting member 117, another end of the second leg supporting member 118 is hinged with the third leg supporting member 119, which in turn is hinged to the frame structure 110. When the second leg supporting member 118 is in a horizontal state, the second leg supporting member 118, the third leg supporting member 119, and the frame structure 110 are in form of in a zigzag shape.

In addition, a positioning rod/bar 122 (see FIGS. 3 and 6) corresponding to the back lifting arm 116 is attached to the back lifting arm 116 and adapted such that when the bed is in a laid back position (i.e., a horizontal position), the positioning bar 122 in cooperation with the back lifting arm 116 is positioned against the upper rail 110a of the frame structure 110 so as to provide further support for the back lifting arm 116. The positioning rod 122 is designed to cooperate with the back lifting arm 116. In one embodiment, the back lifting arm 116 has a channel steel structure or C-shaped steel structure with a downward opening, and the positioning rod 122 has the same structure as the back lifting arm 116. When the back lifting arm 116 is turned to the horizontal state, the position of the back lifting arm 116 is positioned and limited by the positioning rod 122, so as to ensure the back lifting arm 116 is supported the frame structure 110 and to prevent the back lifting arm 116 from turning too low and affecting the user's normal lying down position.

Figure 3:
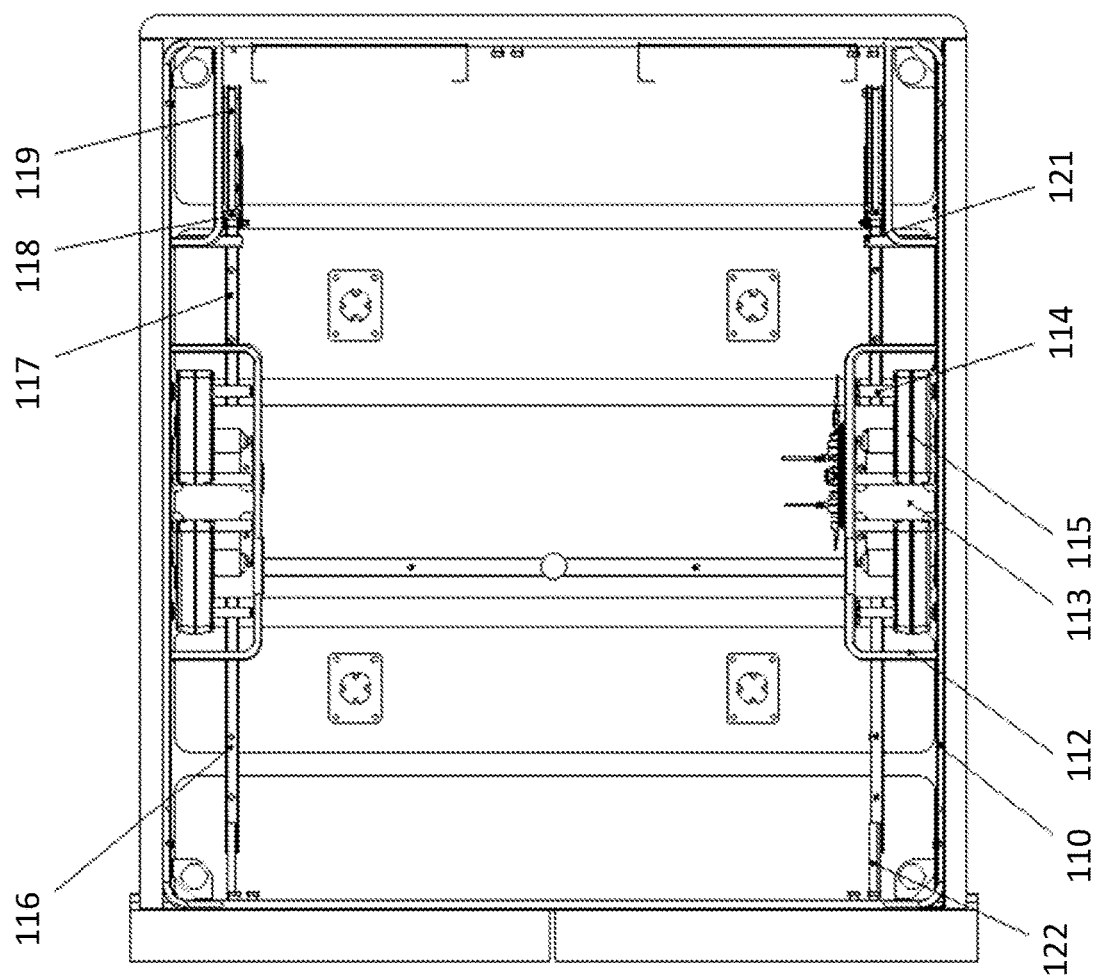
FIG. 3 shows schematically a bottom view of the bed shown in FIG. 1.
Figure 6:
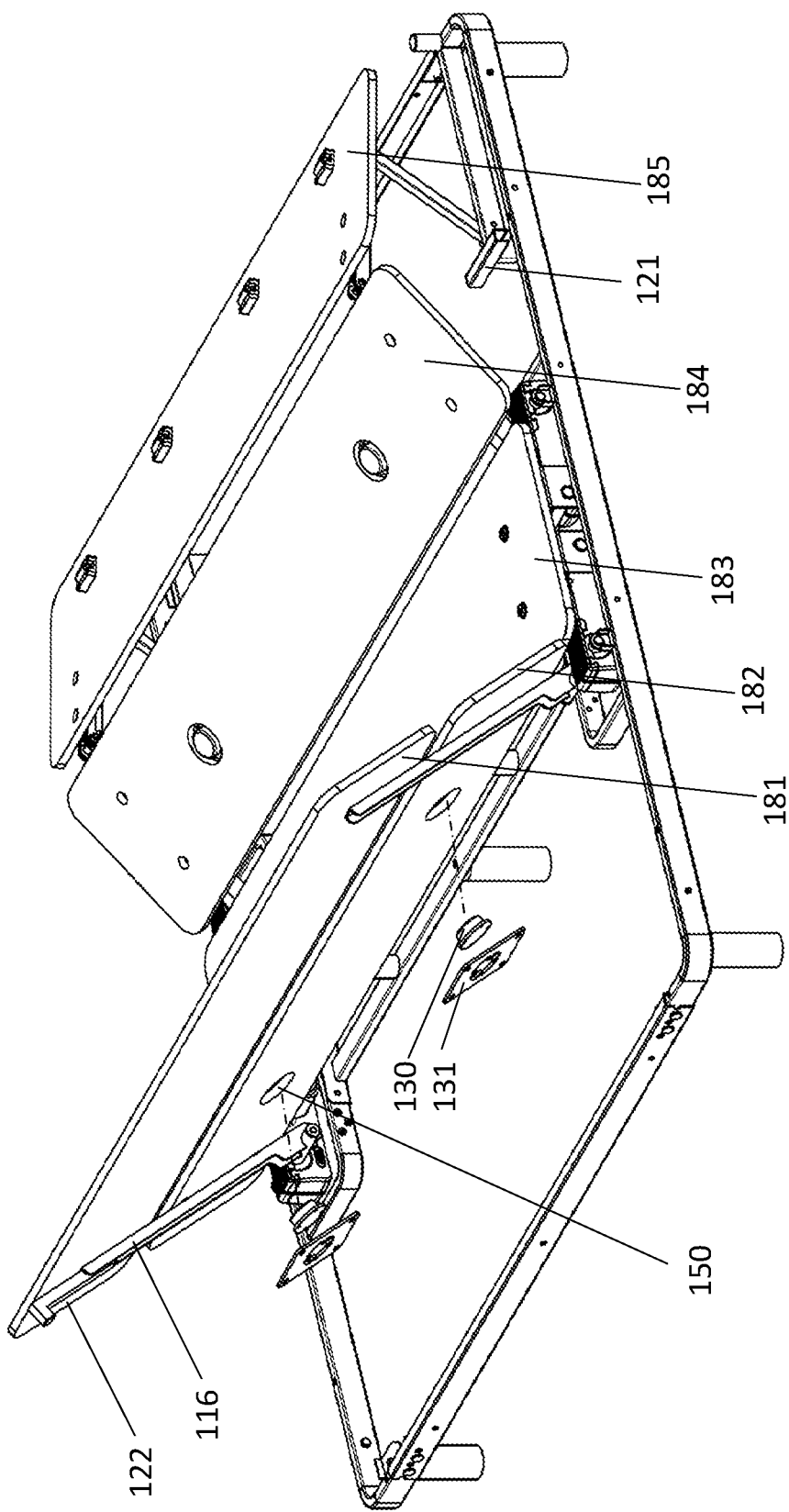
FIG. 6 shows schematically a perspective view of a bed according to one embodiment of the invention.
Figure 7:
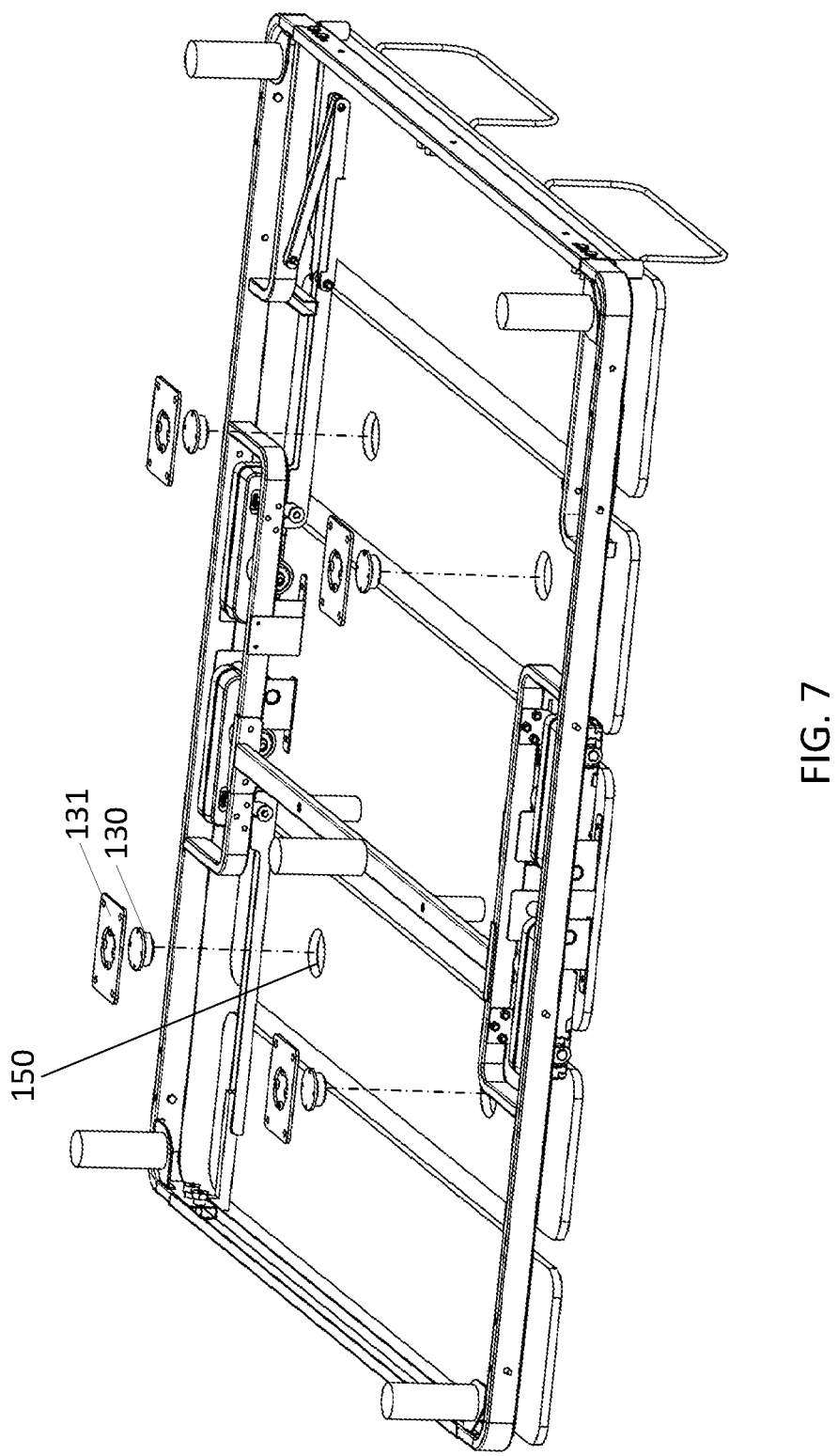
FIG. 7 shows schematically a perspective view of a bed according to one embodiment of the invention.

Further, a supporting bar/rod 121 corresponding to the first leg supporting member 117 is also installed on the frame structure 110, as shown in FIGS. 3 and 5-6. The supporting rod 121 is horizontally arranged and located below the first leg supporting member 117. The support rod 21 is designed to cooperate with the first leg supporting member 117. When the first leg supporting member 117 is turned to the horizontal state, the first leg supporting member 117 is supported by the supporting rod 121 so as to prevent the first leg supporting member 117 from turning too low, and affecting the user's normal lying down position.

In operations, the rotations of the four driving motors 115 in the two installation spaces 113 drive the four rotating rods 114 to rotate accordingly. The rotations of the rotating rods 114 of the back lifting actuator and the leg lifting actuator 115 in turn drive the two back lifting arms 116 and the two first leg supporting members 117 to rotate/flip upward at the same time, the upward flip of the back lifting arms 116 drives the head platform 181 and the back platform 182 to flip upward at the same time, and the upward flip of the first leg supporting member 117 drives the thigh platform 184 to flip upward. When the first leg supporting member 117 is turned upwards, the hinged sides/ends of the second leg supporting member 118 and the first leg supporting member 117 flip upward at the same time, while the other side of the second leg supporting member 118 flips downward due to the presence of the third leg supporting member 119. As such, the turning of the leg platform 185 with one side up and one side down is realized, thereby completing the turning action of the entire bed platforms. In this case, the bed is in an adjusted position. The oppose operation of the four driving motors 115 will position all the platforms in a horizontal state, and the bed is in the laid back position.

Figure 8:
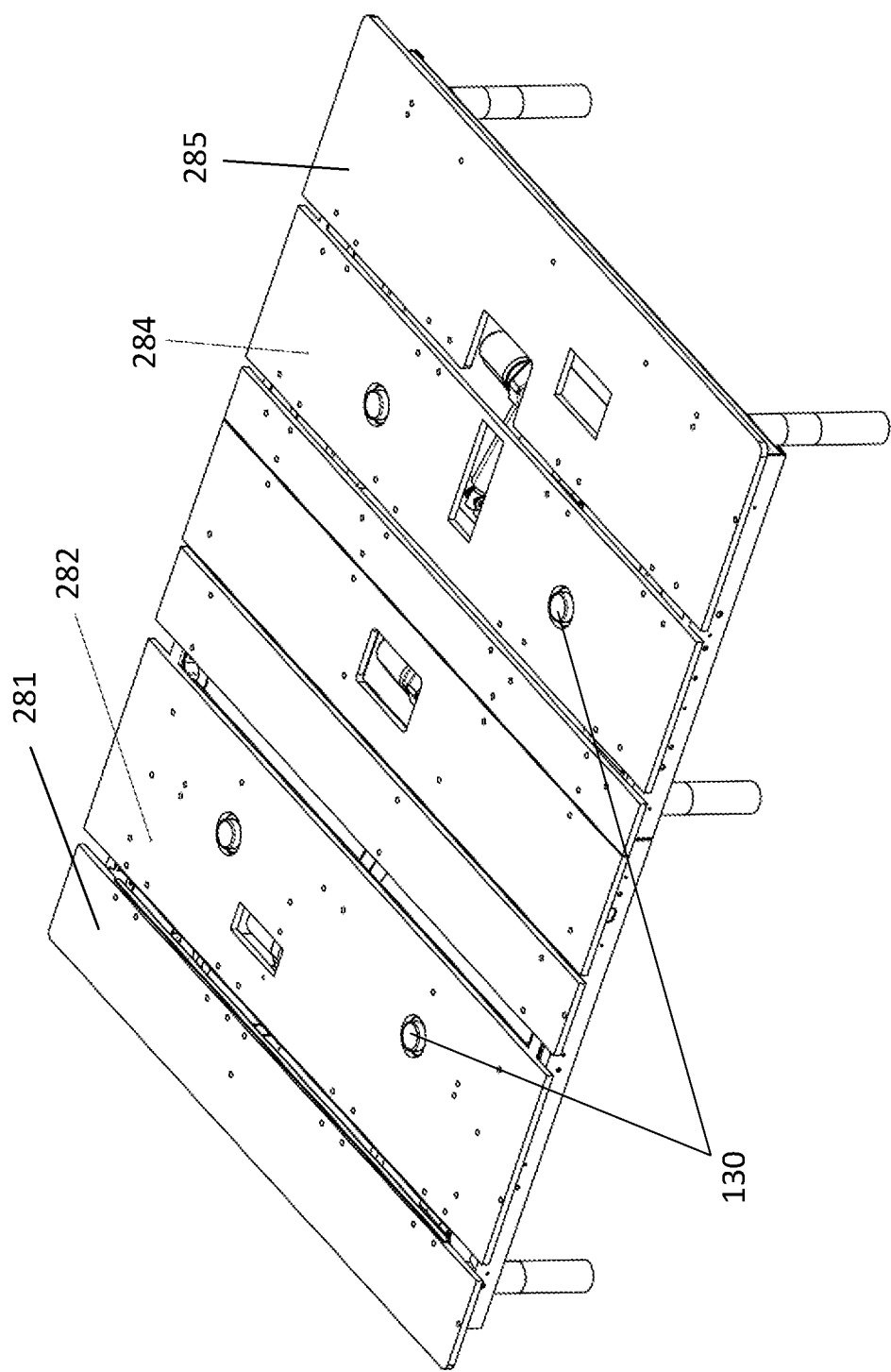
FIG. 8 shows schematically a perspective view of a bed according to one embodiment of the invention.
Figure 9:
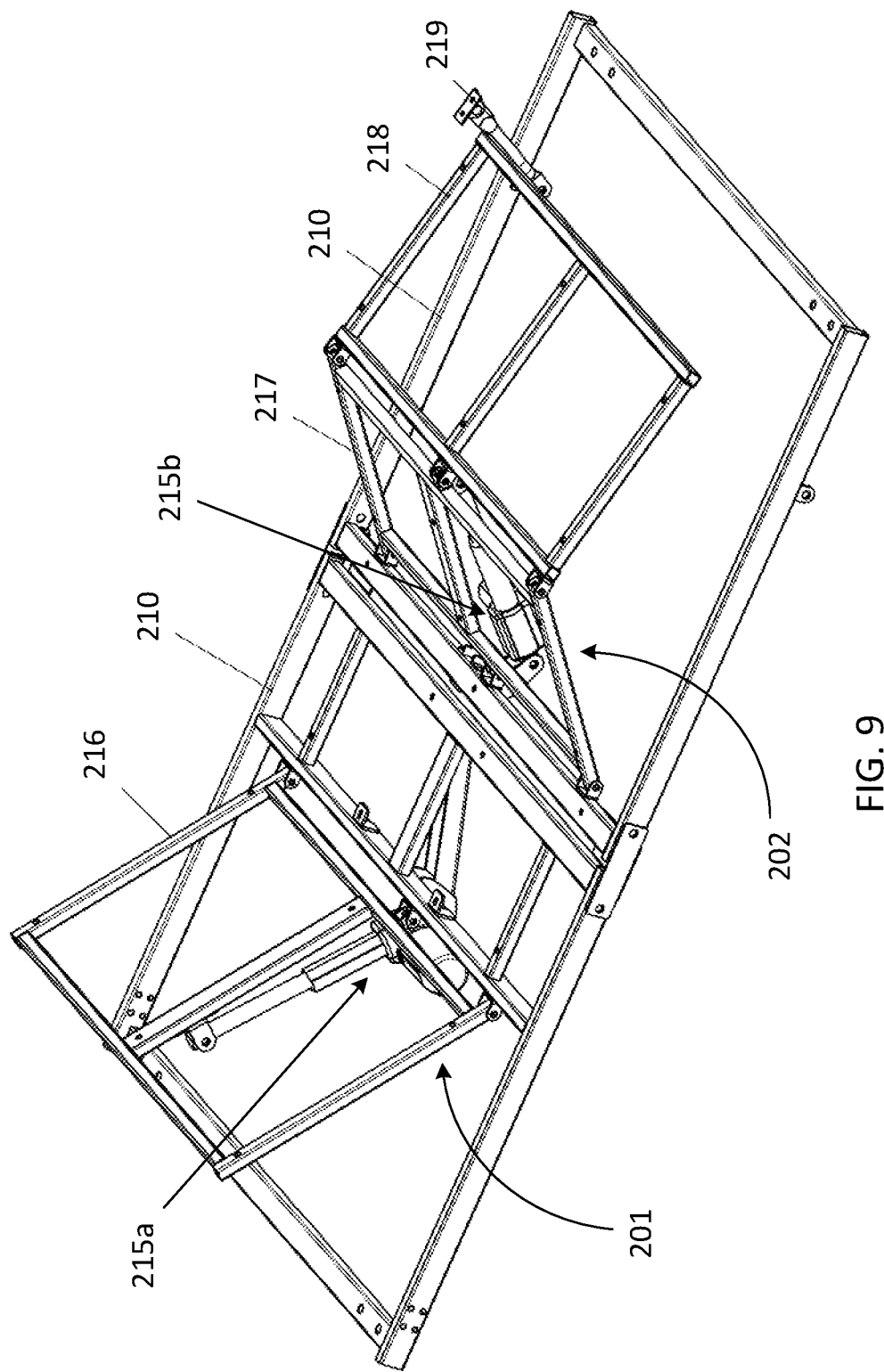
FIG. 9 shows schematically a perspective view of a frame structure and a lifting mechanism of a bed according to one embodiment of the invention.

It should be appreciated that other types of the lifting mechanism can also be used in practice the invention. For example, FIGS. 8-9 show another embodiment of the lifting mechanism used for the bed of the invention. In the exemplary embodiment, the lifting mechanism comprises a back lifting assembly 201 and a leg lifting assembly 202.

The back lifting assembly 201 comprises a back lifting bracket 216 pivotally connected to the frame structure 210, and a back lifting actuator 215a pivotally connected between the back lifting bracket 216 and the frame structure 210 for operably driving the back lifting bracket 216 to pivotally move in an upward rotating direction or a downward rotating direction relative to the frame structure 210, thereby, adjusting the positions of the head and back platforms 281 and 282.

In one embodiment, the back lifting actuator 115a comprises a motor member, an outer tube extending from the motor member, and an activation rod having a first end portion received in the outer tube and an opposite, second end portion. The activation rod is engaged with the motor member and configured to be telescopically movable relative to the outer tube according to a direction of motor rotation. The motor member is pivotally connected to the frame structure 210 and the second end portion of the activation rod pivotally connected to the back lifting bracket. Alternatively, the motor member is pivotally connected to the back lifting bracket and the second end portion of the activation rod pivotally connected to the frame structure 210.

The leg lifting assembly 202 comprises a leg lifting bracket 217 and 218 pivotally connected to the frame structure 210, and a leg lifting actuator 215b pivotally connected between the leg lifting bracket 217 and the frame structure 210 for operably driving the leg lifting bracket 217 and 218 to pivotally move in an upward rotating direction or a downward rotating direction relative to the frame structure 210, thereby, adjusting the positions of the thigh and leg platforms 284 and 285. In the embodiment, a supporting rob 219 has one end pivotally connected the frame structure 210 and another end connected to the bottom of the leg platform 285.

In one embodiment, the leg lifting actuator 115b comprises a motor member, an outer tube extending from the motor member, and an activation rod having a first end portion received in the outer tube and an opposite, second end portion. The activation rod is engaged with the motor member and configured to be telescopically movable relative to the outer tube according to a direction of motor rotation. The motor member is pivotally connected to the frame structure and the second end portion of the activation rod pivotally connected to the leg lifting bracket. Alternatively, the motor member is pivotally connected to the leg lifting bracket and the second end portion of the activation rod pivotally connected to the frame structure.

Figure 10:
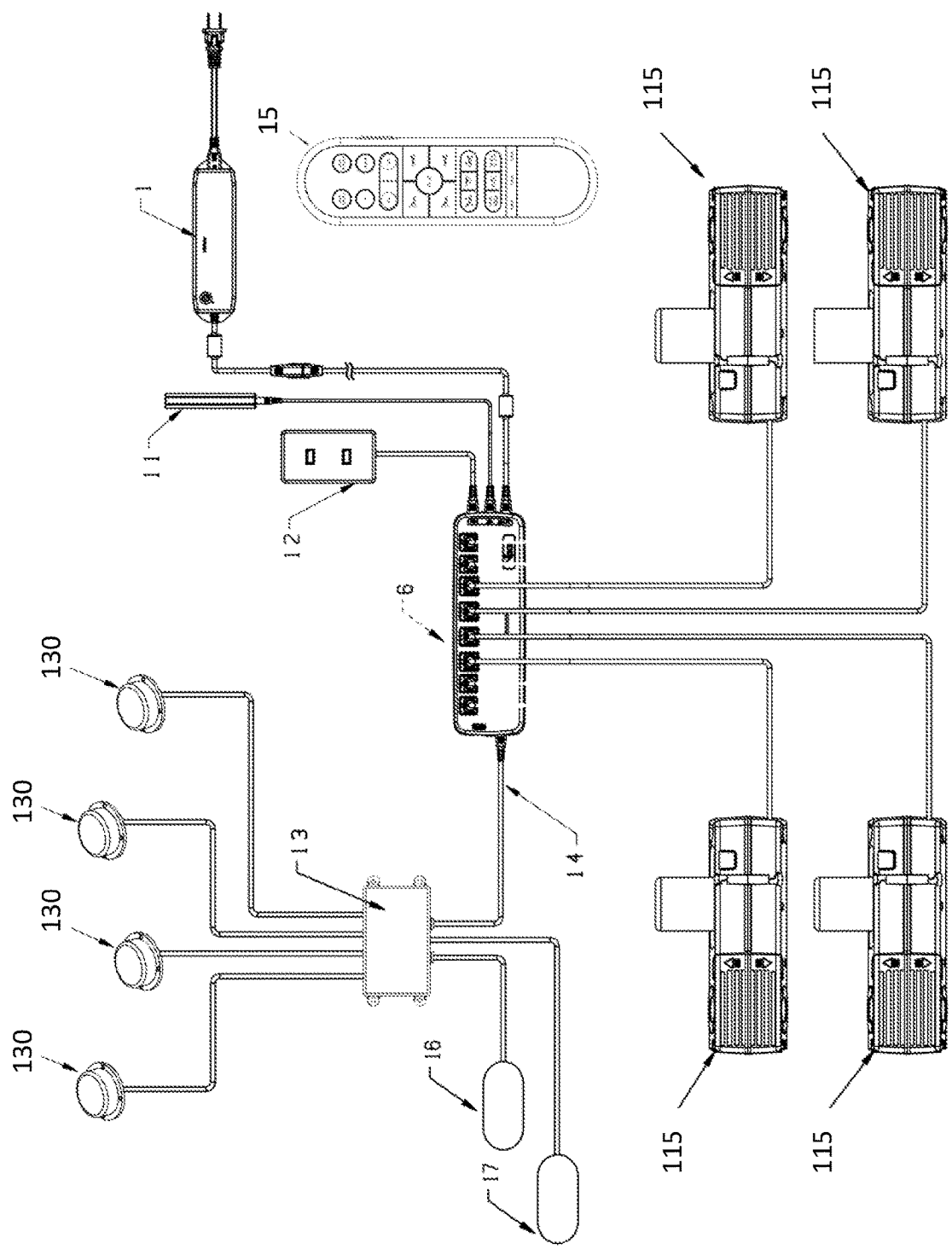
FIG. 10 shows schematically a control system according to one embodiment of the invention.

Referring to FIG. 10, in addition to the music vibrators 130 and the back and leg lifting actuators 115, the bed also includes a control system having a control box 6 and a power supply 1 for power supply to the control box 6. The control box 6 is electrically coupled to the music vibrators 130 and lifting actuators 115 by a plurality of connecting cables 14, or wirelessly, for controlling their operations. Further, the bed may include a number of Bluetooth® speakers 16-17 and a sonic control system 13 electrically coupled with the speakers 16-17 and music vibrators 130. The control box 6 may include internet connection means or protocols for connecting the bed to the internet by wire, or wirelessly. The operations of the music vibrators 130, the speakers 16-17 and the back and leg lifting actuators 115 of the bed can be initiated and controlled by a remote control 15, or an APP using in smart mobile devices, such as smart phones, smart watches, tablets, or the likes.

For example, through the buttons on the remote control 15, the music vibrators 130 can be activated to generate vibrations directly according to the preset frequency and cycle. Alternatively, the user can also use the Bluetooth® speaker 16-17 to connect to an electronic device to play music. In the case, the music vibrators 130 follow the music rhythm to generate vibrating waves accordingly, and the vibrating waves in turn drives the mattress to produce a sense of vibrations, thereby, giving the use the massage effect with the music rhythm.

The user can adjust the bed position by the remote control 15 or an APP using in a smart mobile device.

In addition, the bed may also have LED lights 11 and USB ports 12 electrically coupled to the control box 6. LED lights 15 can be employed to indicate the working conditions of the music vibrators 130, the back and leg actuators 115. For example, when the music vibrators 130 are working, the LED lights 15 are turned on and emit color light, or change colors in according with the music rhythm. The USB ports 16 are set for interfacing with the control box 10 by the user when needed.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

What is claimed is:

1. A bed, comprising:
   a frame structure;
   a plurality of platforms disposed on the frame structure; and
   one or more massage devices spatial-separately installed on the plurality of platforms, wherein each massage device comprises a sonic vibrator that is accommodated in an opening defined in a respective platform of the plurality of platforms through a transition piece fixed on a respective platform, wherein the transition piece has a through hole and one or more protrusions on an inner wall of the through hole, and wherein the sonic vibrator has a bottom flange mounted on the one or more protrusions of the transition piece.

2. The bed of claim 1, wherein the one or more massage devices are operable individually or cooperatively.

3. The bed of claim 2, wherein the one or more massage devices are operable with a remote control, and/or a smart mobile device.

4. The bed of claim 1, wherein the transition piece is capable of vibrating up and down with the sonic vibrator.

5. The bed of claim 4, wherein the transition piece is an elastic soft plate formed of rubber or silicone, or a hard thin sheet formed of aluminum, steel, or wooden composite.

6. The bed of claim 1, further comprising:
a lifting mechanism positioned between the frame structure and the plurality of platforms for operably adjusting positions of at least one of the plurality of platforms so as to adjust the bed at a desired position.

7. The bed of claim 6, wherein the lifting mechanism comprises a back lifting assembly and a leg lifting assembly,
wherein the back lifting assembly comprises a back lifting bracket pivotally connected to the frame structure, and a back lifting actuator pivotally connected between the back lifting bracket and the frame structure for operably driving the back lifting bracket to pivotally move in an upward rotating direction or a downward rotating direction relative to the frame structure; and
wherein the leg lifting assembly comprises a leg lifting bracket pivotally connected to the frame structure, and a leg lifting actuator pivotally connected between the leg lifting bracket and the frame structure for operably driving the leg lifting bracket to pivotally move in an upward rotating direction or a downward rotating direction relative to the frame structure.

8. The bed of claim 7, wherein the back lifting actuator comprises a motor member, an outer tube extending from the motor member, and an activation rod having a first end portion received in the outer tube and an opposite, second end portion, wherein the activation rod is engaged with the motor member and configured to be telescopically movable relative to the outer tube according to a direction of motor rotation, wherein the motor member is pivotally connected to the frame structure and the second end portion of the activation rod pivotally connected to the back lifting bracket, or wherein the motor member is pivotally connected to the back lifting bracket and the second end portion of the activation rod pivotally connected to the frame structure.

9. The bed of claim 7, wherein the leg lifting actuator comprises a motor member, an outer tube extending from the motor member, and an activation rod having a first end portion received in the outer tube and an opposite, second end portion, wherein the activation rod is engaged with the motor member and configured to be telescopically movable relative to the outer tube according to a direction of motor rotation, wherein the motor member is pivotally connected to the frame structure and the second end portion of the activation rod pivotally connected to the leg lifting bracket, or wherein the motor member is pivotally connected to the leg lifting bracket and the second end portion of the activation rod pivotally connected to the frame structure.

10. The bed of claim 6, further comprising a controller configured to control operations of the one or more massage devices and the lifting mechanism so as to provide massage effect from the one or more massage devices and/or adjust positions of the at least one of the plurality of platforms.

11. A bed, comprising:
a frame structure;
a plurality of platforms disposed on the frame structure;
one or more massage devices spatial-separately installed on the plurality of platforms, wherein each massage device comprises a sonic vibrator; and
a lifting mechanism positioned between the frame structure and the plurality of platforms for operably adjusting positions of at least one of the plurality of platforms so as to adjust the bed at a desired position, wherein the lifting mechanism comprises a pair of lifting assemblies, wherein each lifting assembly comprises:
a bracket mounted on the frame structure;
a back lifting arm and a leg lifting mechanism; and
a back lifting actuator and a leg lifting actuator received in the bracket, wherein each of the back and leg lifting actuators comprises a driving shaft and a motor member engaged with the driving shaft for driving the driving shaft to rotate,
wherein the driving shaft of the back lifting actuator is engaged with the back lifting arm for operably adjusting the back lifting arm at desired back positions, and
wherein the driving shaft of the leg lifting actuator is engaged to the leg lifting mechanism for operably adjusting the leg lifting mechanism at desired leg positions.

12. The bed of claim 11, further comprising:
a positioning bar attached to the back lifting arm and adapted such that when the bed is in a laid back position, the positioning bar is in cooperation with the back lifting arm and is positioned against the frame structure so as to provide support thereto.

13. The bed of claim 11, wherein the leg lifting mechanism comprises first, second, and third leg supporting members, wherein the first leg supporting member is connected to the driving shaft of the leg lifting actuator, the second leg supporting member is pivotally connected to the first leg supporting member, the third leg supporting member is pivotally connected to the second leg supporting member and the frame structure.

14. The bed of claim 13, further comprising:
at least one supporting bar attached to the frame structure and corresponding to the first leg supporting member, such that when the bed is in a laid back position, the at least one supporting bar is against the first leg supporting member so as to provide support thereto.

15. The bed of claim 13, wherein the plurality of platforms comprises:
a seat platform mounted on tops of the brackets of the pair of lifting assemblies;
at least one back platform coupled with the back lifting arm, such that the at least one back platform is operably rotatable around its lower edge in a back platform downward rotating direction or a back platform upward rotating direction; and
a thigh platform and a leg platform coupled to the leg lifting mechanism, such that the thigh platform is rotatable around its upper edge in a thigh platform downward rotating direction or a thigh platform upward rotating direction, and the leg platform is rotatable around its upper edge in a leg platform downward rotating direction or a leg platform upward rotating direction.

\* \* \* \* \*